United States Patent [19]

Noto et al.

[11] Patent Number: 5,155,026

[45] Date of Patent: Oct. 13, 1992

[54] METHOD FOR DETERMINATION OF NAGASE AND REAGENT THEREFOR

[75] Inventors: Akira Noto, Osaka; Kunihiro Nakajima; Kazuyuki Sasakura, both of Nara; Tsutomu Sugasawa, Hyogo, all of Japan

[73] Assignee: Shionogi & Co., Ltd., Osaka, Japan

[21] Appl. No.: 723,652

[22] Filed: Jun. 26, 1991

[30] Foreign Application Priority Data

Jun. 11, 1987 [JP] Japan ................................ 62-146143

[51] Int. Cl.$^5$ ............................................. C12Q 1/34
[52] U.S. Cl. ..................................... 435/18; 435/810; 536/17.2
[58] Field of Search .................. 435/18, 810; 536/17.2

[56] References Cited

U.S. PATENT DOCUMENTS

| 4,433,139 | 2/1984 | Ogawa et al. | 536/17.2 |
| 4,552,841 | 11/1985 | Ogawa et al. | 435/18 |
| 4,754,025 | 6/1988 | Makise et al. | 536/17.7 |

FOREIGN PATENT DOCUMENTS

| 0060793 | 9/1982 | European Pat. Off. |
| 0097506 | 1/1984 | European Pat. Off. |
| 0180961 | 5/1986 | European Pat. Off. |

OTHER PUBLICATIONS

"Table 44. Properties of Common Indicators" Grant and Hackh's Chemical Dictionary p. 302 (1987).

Primary Examiner—Esther L. Kepplinger
Assistant Examiner—Carol E. Bidwell
Attorney, Agent, or Firm—Wenderoth, Lind & Ponack

[57] ABSTRACT

Highly sensitive reagent for colorimetrically determining N-acetyl-$\beta$-D-glucosaminidase (NAGase) activity by the continuous method, comprising sodio-3,3'-dichlorophenolsulfonphthaleinyl N-acetyl-$\beta$-D-glucosaminide and a buffer, with which renal dysfunction can be diagnosed precisely, quickly, and easily.

7 Claims, 1 Drawing Sheet

METHOD FOR DETERMINATION OF NAGASE AND REAGENT THEREFOR

This application is a continuation of now abandoned application Ser. No. 07/190,818 filed on May 6, 1988.

BACKGROUND OF INVENTION

1. Field of the Invention

The present invention provides kits for determination of N-acetyl-β-D-glucosaminidase (hereinafter referred to as NAGase) activity, which is one of the important markers of renal dysfunction and methods for determining the activity by using them.

2. Prior Art

4-Methylumbelliferyl N-acetyl-β-D-glucosaminide (hereinafter referred to as 4MU-NAG) and p-nitrophenyl N-acetyl-β-D-glucosaminide (hereinafter referred to as PNP-NAG) have long been known as substrates for determining NAGase activity. The methods by using them have, however, such disadvantages that they require urine blanks and substrate blanks in each test, they are liable to be affected by inhibitors in urine, and they need a long time for the determination.

Sodio-meta-cresolsulfonphthaleinyl N-acetyl-β-D-glucosaminide (hereinafter referred to as MCP-NAG), wherein meta-cresolsulfonphthaleine (hereinafter referred to as MCP) is a color indicator, was developed and disclosed in KOKAI 58-994 as a substrate capable of reducing such disadvantages as above. It still has, however, disadvantages in that it requires a substrate blank and a terminating step to determine NAGase activities with addition of an alkaline agent (one-point method).

Recently, 2-chloro-4-nitrophenyl-N-acetyl-β-D-glucosaminide (hereinafter referred to as CNP-NAG) was developed and disclosed in KOKAI 61-112092 as a reagent for determining NAGase activity without termination of the reaction (continuous method). In this method, enzyme activity is monitored continuously and the method can be easily adapted to automatic analysers. This still has a disadvantage, however, in that it takes several minutes to dissolve CNP-NAG completely, even in the presence of surfactants, because the substrate is hardly soluble in water. Further, it takes much time to determine the activity of a trace amount of NAGase.

SUMMARY OF INVENTION

The present invention provides kits for determining NAGase activity comprising the following reagents (a) and (b) with practically no alkaline reagent:

(a) a substrate reagent containing sodio-3,3'-dichlorophenol-sulfonphthaleinyl N-acetyl-β-D-glucosaminide (hereinafter referred to as CPR-NAG) of the formula:

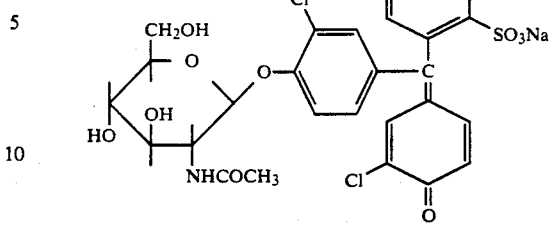

and (b) a buffer reagent.

Linear Regression: Y=0.97x+1.84

Coefficient of Correlation: r=0.99

Figure 3:
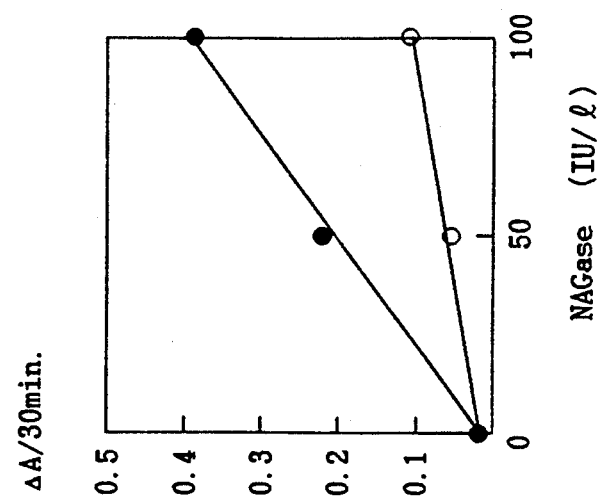

FIG. 3 shows calibration curves on the CPR-NAG method (the present invention) and the CNP-NAG method (prior art). The axis of abscissa indicates concentration of NAGase (IU/l) and the axis of ordinate indicates increase of absorbance in 30 minutes, wherein the curve ●—● is for the CPR-NAG method ($\Delta A_{540nm}$/min.) and ○—○ for the CNP-NAG method ($\Delta A_{405nm}$/min.).

DESCRIPTION OF PREFERRED EMBODIMENT

Problem to be Resolved

The present inventors have tried to resolve the problem and achieved the present invention providing a new substrate, high solubility and ease of handling. The kits of the present invention require no urine blank and can determine the activity by the continuous method. Furthermore, the determination of NAGase activity can be performed precisely and quickly even in a case of a very small amount of NAGase, since the present method has a very high sensitivity.

Means to Resolve the Problem

Sodio-3,3'-dichlorophenolsulfonphthaleinyl N-acetyl-β-D-glucosaminide (CPR-NAG) used in the present invention can readily be prepared from 3,3'-dichlorophenolsulfonphthalein (CPR) and 1-chloro-1-deoxy-2,3,4,6-tetraacetyl-α-D-glucosamine, according to the process disclosed in KOKAI 58-994.

Unlike CNP-NAG, the aforementioned CPR-NAG is freely and quickly soluble in water and, therefore, no specific additives such as surfactants are needed. Accordingly, substrate solutions can be prepared very quickly.

It is very important to stabilize substrates, because decomposition of them makes the measurable limitation of enzyme activities narrower. CPR-NAG used in the present invention is fairly stable even in the absence of any stabilizers, and therefore, it may be formulated as it is. Further, it can be stored in a refrigerator for a long period of time, without decreasing the measurable limitation. Borax may be added to it as a stabilizer, if much longer shelf-life is desired. Borax may be added to one part of CPR-NAG at an amount of about 0.02 to about 2.0 parts, more preferably at about 0.6 to 1.2 parts.

In formulating the reagents into a kit, the substrate reagent and the buffer reagent may be prepared as either separate formulations or a single formulation. It is recommended to prepare the formulation as lyophilizate in view of its appearance and stability.

Although NAGase shows maximum activity at pH about 4.5 to about 5.0, the apparent reaction rate becomes maximum at the pH about 6.25 in the present invention using CPR-NAG. Accordingly, any buffer reagent may be used as long as it can keep the reaction pH in a range between about 4.5 and about 8.0. More preferably, buffers which can keep the pH between about 6.0 and 6.5, and most preferably, those which can keep the pH between about 6.2 and 6.3 may be used. For example, a citrate buffer, a borax-citrate buffer, a citrate-phosphate buffer, a phosphate buffer, a borax-phosphate buffer, a sodium barbitate-sodium acetate buffer, Good's buffer and the like may be used.

In the method using the aforementioned MCP-NAG, the enzyme should be well reacted with the substrate and an alkaline reagent should be added for enzyme inactivation and color development. This method requires such additional step in comparison with the present method. Further, since the color development can not be observed as the reation proceeds, the determination might have to be repeated again if an alkaline reagent is added at the time before the reaction proceeds well.

On the other hand, it is easy to determine the activity by using the kit of the present invention without such a mistake as aforementioned, because the proceeding of the enzyme reaction can be traced directly by the change of the absorbance. As most recent analytical instruments are designed for continuous methods, it is quite easy to determine the enzyme activity automatically.

Principle of Measurement

The substrate reagent CPR-NAG is hydrolyzed by NAGase to give CPR in a buffer solution at pH about 4.5–8.0. The resulting CPR, whose pKa is about 5.8, develops reddish purple immediately. NAGase activity is determined by the changes of absorbance with the lapse of a unit time.

Procedure for Continuous Method

To 1.0 ml of a substrate buffer (2–6 mM CPR-NAG, pH about 4.5–8.0) is added 50 μl of a test sample*. The absorbances $A^1$ and $A^2$ of the mixed solution at a wavelength of 575 nm are measured by a spectrophotometer equipped with constant-temperature cell at time $t^1$ and time $t^2$, respectively, after addition of the test sample.

Note: The test sample* means urine or serum collected from human or animals, which is preferably measured immediately after the collection. When preservation for a long period is needed, it is recommended that the sample pH is adjusted to 6.5 with 2N-HCl or 2N-KOH. Under such a condition, NAGase activity in the test sample is stable for one day at room temperature and for 4 months at $-20°$ C.

Definition of the Enzyme Activity

Under a measuring condition, the amount of NAGase capable of giving 1 μM of CPR per minute is defined to be 1 IU.

Calculation of the Enzyme Activity

NAGase activity can be calculated according to the following equation.

$$\text{NAGase}(IU/l) = \frac{\Delta A \times 1.05}{\epsilon \times d} \times \frac{1}{t^2 - t^1} \times \frac{1000}{0.05}$$

$\Delta A = A^2 - A^1$
$\epsilon =$ the extinction coefficient (cm$^2$/μM) of CPR at the pH and wavelength employed
$d =$ the length of optical path (cm)

$\Delta t$, i.e. ($t^2 - t^1$) is normally 1 to 20 minutes and preferably 5 to 10 minutes.

The present invention is explained in more detail by the following Examples and Experiments, which are not intended to limit the scope of this invention.

PREPARATION 1

Preparation of 3,3'-dichlorophenolsulfonphthaleinyl N-acetyl-β-D-glucosaminide pentaacetate (1)

To a stirred solution of chlorophenol red (1.4 g, 3.3 mmol) in methanol (4 ml) is added sodium methoxide (6.8 ml, 3.3×2 mmol) and the solution is stirred for further 15 minutes. The solvent is removed under reduced pressure below 35° C. and the resulting residue is triturated with toluene and the solvent is removed under reduced pressure. After repeated co-distillation with toluene (×2), the residue is dried under reduced pressure.

To a solution of the disodium salt obtained above in 7 ml of dimethylformamide (DMF) is added acetochloroglucosamine (1.1 g, 3 mmol) and the solution is stirred for 21 hours. Then the solution is combined with 10 ml of Amberlite® IRC-50 (Rohm & Hass Co.) and the resulting mixture is stirred for 30 minutes. The resin is filtered and washed with methanol. The filtrates and washings are collected and evaporated to dryness.

The residue is dissolved in pyridine (20 ml) followed by adding acetic anhydride (10 ml) and the solution is allowed to stand at room temperature overnight. After removal of the solvent and reagent in vacuo, toluene is added to the residue and the solution is evaporated again to dryness in vacuo. The residue is chromatographed on silica gel (10 g of SiO$_2$ containing 3% water, 0.063–0.2 mmφ) to give 2.1 g of a colorless gummy matter from the dichloromethane fractions (160 ml). This is purified again on column chromatography (Lober B, solvent system: acetic acid) to give 0.98 g of the objective compound as the fourth to ninth fractions (15 g per fraction). This is recrystallized from ethyl acetate/ether to give 0.8 g (36.9% yield) of the captioned compound (1), mp. 142°–143° C.

IR ν max(Nujol): 3265, 3090, 1750, 1663, 1604, 1556, 1352 cm$^{-1}$.

NMR (90 MHz, CDCl₃)δ: 1.85(3H, s), 2.00(9H, s), 2.32(3H, s).

Elementary Analysis Calcd. for C₃₅H₃₃NO₁₄Cl₂S.½H₂O: C; 52.32, H; 4.27, N; 1.74, Cl; 8.83, S; 3.99.

Found: C; 52.33, H; 4.25, N; 1.73, Cl; 8.34, S; 3.84.

PREPARATION 2

Preparation of sodio-3,3'-dichlorophenolsulfonphthaleinyl N-acetyl-β-D-glucosaminide (2)

To a stirred solution of 2.057 g (2.56 mmol) of the compound (1) prepared in Preparation 1 in 18 ml of methanol is added a solution of 0.971M sodium methoxide (2.58×2 mmol) in methanol (5.3 ml). After standing for 3 hours under nitrogen atmosphere, Amberlite® IRC-50 (10 ml) is added and the mixture is stirred for an hour, then the resin is filtered and washed with methanol. The filtrates and washings are collected and evaporated to dryness in vacuo at a temperature below 35° C. to give yellow foam. This is dissolved in 5 ml of water, chromatographed on DEAE-Sepharose® CL-6B (10 ml; Pharmacia Co.), and fractions are collected. The fractions are lyophilized to give 1.735 g (98.1% yield) of the objective compound (2) as amorphous powder.

Elementary Analysis Calcd. for C₃₅H₃₃NO₁₄Cl₂S.½H₂O: C; 49.24, H; 4.28, N; 2.03, Cl; 10.26, S; 4.64.

Found: C; 48.87, H; 4.61, N; 2.05, Cl; 9.81, S; 4.38.

EXAMPLE 1

CPR-NAG is dissolved in water containing 50 mM borax to prepare an aqueous solution containing 30 mM CPR-NAG, 2 ml each of which is placed in 20 ml glass vials and lyophilized to give a substrate reagent.

Dipotassium citrate (502.9 g) and 1014.0 g of potassium citrate are ground into powder, mixed together, uniformed in particle size, 304.4 mg each of which is then placed in a 25 ml plastic bottle to give a buffer reagent.

Distilled water (20 ml) is added to the buffer reagent to prepare a buffer solution, which is then added to the substrate reagent to give a reagent solution (pH 6.25).

EXAMPLE 2

In 500 mM (pH 6.10) of a Bis-Tris* buffer solution are dissolved 30 mM CPR-NAG, 50 mM borax, and 1.5M sodium chloride and the solution is placed in a 20 ml glass vial by 2 ml each and then lyophilized to give a reagent for measurement containing a buffer reagent.

NOTE) Bis-Tris* means bis(2-hydroxyethyl)iminotris(hydroxymethyl)methane.

Distilled water (20 ml) is added thereto to give a reagent solution for measurement (pH 6.25).

EXAMPLE 3

In 500 mM potassium citrate buffer (pH. 5.84) are dissolved 30 mM CPR-NAG and 50 mM borax, and the solution is divided into 1.1 ml portions which are placed in 14 ml glass vials and are lyophilized to give a substrate.

Then 11 ml of distilled water to the lyophilized substrate to give a substrate solution (pH 6.25).

EXPERIMENT 1

In each well of a 96-well flat-bottomed micro titerplate is placed 100 μl of the reagent solution (pH 6.25) prepared in Example 1 and 10 μl each of a test sample is added thereto. The absorbance A¹ at the wavelength of 540 nm is measured by a microplate spectrophotometer (type MCC 340, Titertech Co.). Samples tested are allowed to stand at room temperature and, in precisely ten minutes, A² at 540 nm is measured again.

Absorbances (ΔB=B²−B¹) of blank, which is prepared by adding 10 μl of distilled water in place of the test sample, are measured in the same manner as above.

In the same manner as in the test sample, a calibration curve is illustrated from the absorbances on the NAGase specimen having a known activity. NAGase activity is calculated from the changes of absorbance per minute.

$$\Delta A \text{ min}^{-1} = \frac{(A^2 - A^1) - \Delta B}{10}$$

Figure 2:
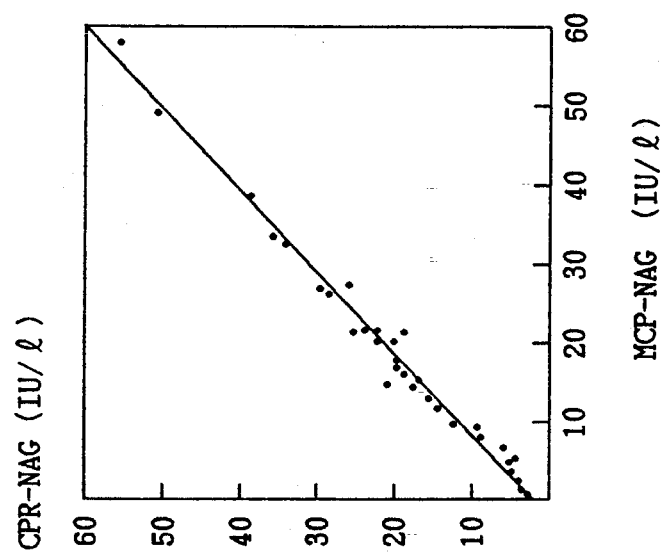
FIG. 2 shows correlation between the MCP-NAG method and the CPR-NAG method of the present invention. The axes of abscissa and of ordinate indicate NAGase concentrations (IU/l) obtained by the MCP-NAG method and the CPR-NAG method, respectively.
Figure 1:
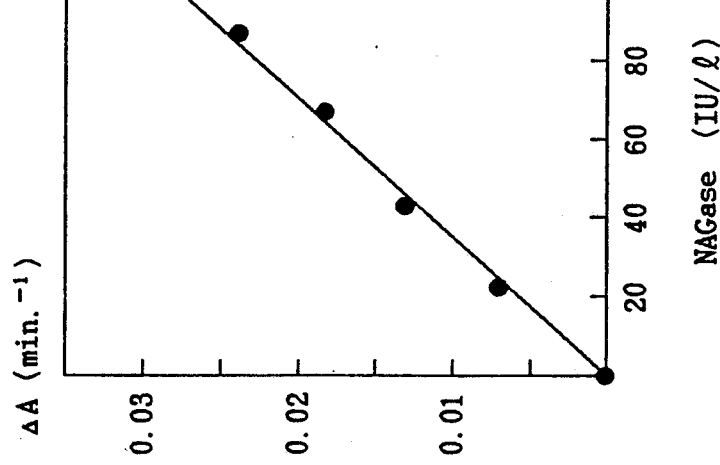
FIG. 1 is a calibration curve obtained by the present invention which is illustrated from the data on NAGase with known activity and shows the relationship between the NAGase activity and 3,3'-dichlorophenolsulfonphthalein (chlorophenol red: hereinafter referred to as CPR) yielded. The axis of abscissa indicates concentrations of NAGase (IU/l) and the axis of ordinate indicates the production rate of CPR by the absorbance ($\Delta A_{540nm}$/min.).

FIG. 1 shows the calibration curve and FIG. 2 shows correlation between method by the present invention and one-point method by the conventional MCP-NAG (NAG Test Shionogi: trade name).

EXPERIMENT 2

Using a commercialy available kit for NAGase activity (CNP-NAG continuous method), the reagent solution is prepared according to the recommended usage. The reagent solution (50 μl each) is placed in wells of a 96-well flat-bottomed micro titerplate. To the wells is also added 10 μl each of standard solution of NAGase with known activity. The absorbance A¹ at the wavelength of 405 nm is measured by a microplate spectrophotometer (type MCC 340, Titertech Co.). Samples tested are allowed to stand at room temperature and, in precisely 30 minutes, A² at 405 nm is measured again to illustrate a calibration curve (○−○) for the CNP-NAG method (FIG. 3).

The reagent solution (100 μl each, pH 6.25) prepared in Example 1 is placed in wells of a 96-well flat-bottom micro titerplate and the test sample is also added thereto by 10 μl each. The absorbance A¹ at 540 nm is measured by a microplate spectrophotometer (type MCC 340, Titertech Co.). Samples tested are allowed to stand at room temperature and, in precisely 10 minutes, A² at 540 nm is measured to illustrate a calibration curve (●−●) for the CPR-NAG method of the present invention (FIG. 3).

As clearly understood from FIG. 3, the method of the present invention is approximately 3 to 4 times more sensitive compared with the conventional method. If the concentration of NAGase is very low, methods with low sensitivities require a long period of time to give a precise determination, while those with high sensitivities such as the present invention, can give a precise determination in a very short time. This is an advantage.

What is claimed is:

1. A kit for determining N-acetyl-β-D-glucosaminidase activity consisting essentially of the following reagents (a) and (b):
    (a) a substrate reagent containing sodio-3,3'-dichlorophenolsulfonphthaleinyl N-acetyl-β-D-glucosaminide of the formula:

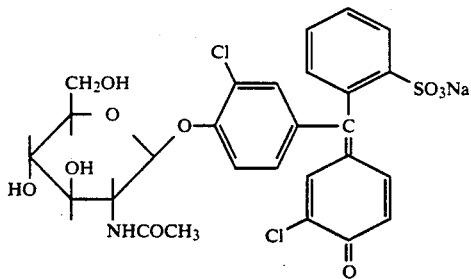

(b) a buffer reagent selected from the group consisting of citrate buffer and borax-citrate buffer.

2. The kit claimed in claim 1, wherein said reagents (a) and (b) are placed together in a single container.

3. The kit claimed in claim 2, comprising a lyophilized mixture of sodio-3,3'-dichlorophenolsulfonphthaleinyl N-acetyl-β-D-glucosaminide, borax, and said buffer reagent.

4. The kit claimed in claims 2 or 3, wherein said buffer reagent is a citrate buffer.

5. The kit claimed in claim 1, wherein said reagents (a) and (b) each is placed in individual containers.

6. The kit claimed in claim 5, wherein said substrate reagent (a) is a lyophilized mixture of sodio-3,3'-dichlorophenolsulfonphthaleinyl N-acetyl-β-D-glucosaminide and borax.

7. A method for determining N-acetyl-β-D-glucosaminidase activity which comprises dissolving a reagent containing sodio-3,3'-dichlorophenolsulfonphthaleinyl N-acetyl-β-D-glucosaminide of the following formula:

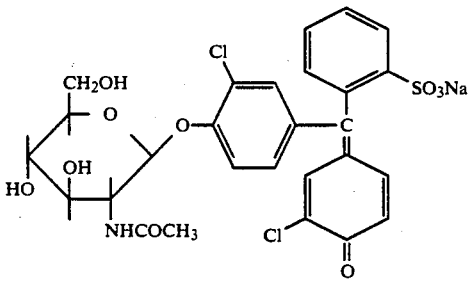

in a buffer selected from the group consisting of citrate buffer and borax-citrate buffer to give a substrate solution of pH 6.0 to pH 6.5, adding a test sample to the substrate solution, and colorimetrically measuring the resulting 3,3'-dichlorophenolsulfonphthalein continuously.

* * * * *